United States Patent
Noda et al.

(10) Patent No.: US 10,035,974 B2
(45) Date of Patent: Jul. 31, 2018

(54) CLEANING AGENT FOR WASHING OUT SILICONE STAIN

(71) Applicants: KANEKA CORPORATION, Osaka-shi, Osaka (JP); NATIONAL INSTITUTE OF ADVANCED INDUSTRIAL SCIENCE AND TECHNOLOGY, Tokyo (JP)

(72) Inventors: Koji Noda, Tokyo (JP); Masashi Izumida, Takasago (JP); Satohiro Yanagisawa, Tokyo (JP); Tohru Nakashima, Settsu (JP); Takuto Nagano, Osaka (JP); Toshiaki Taira, Tsukuba (JP); Tomohiro Imura, Tsukuba (JP); Dai Kitamoto, Tsukuba (JP)

(73) Assignees: KANEKA CORPORATION, Osaka-Shi (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 345 days.

(21) Appl. No.: 14/778,685

(22) PCT Filed: Mar. 25, 2014

(86) PCT No.: PCT/JP2014/058228
§ 371 (c)(1),
(2) Date: Sep. 21, 2015

(87) PCT Pub. No.: WO2014/157169
PCT Pub. Date: Oct. 2, 2014

(65) Prior Publication Data
US 2016/0046890 A1 Feb. 18, 2016

(30) Foreign Application Priority Data
Mar. 25, 2013 (JP) .................................. 2013-062835

(51) Int. Cl.
*C11D 1/10* (2006.01)
*B05D 3/00* (2006.01)
*C07K 7/56* (2006.01)
*B08B 3/10* (2006.01)

(52) U.S. Cl.
CPC ................ *C11D 1/10* (2013.01); *B05D 3/002* (2013.01); *B08B 3/10* (2013.01); *C07K 7/56* (2013.01)

(58) Field of Classification Search
None
See application file for complete search history.

(56) References Cited

U.S. PATENT DOCUMENTS 6,319,898 B1 * 11/2001 Davies ..................... C12Q 1/02
435/15
6,838,426 B1 * 1/2005 Zeilinger ............... C11D 1/528
510/238

(Continued)

FOREIGN PATENT DOCUMENTS

JP 6-16534 A 1/1994
JP 2003-155207 A 5/2003

(Continued)

OTHER PUBLICATIONS

Paul C. Lanteri, Sealant Joint Rehabilitation: More Than a Quick Fix, Journal of architectural technology, Issue 2, vol. 21, No. 2, 2003, pp. 1-8.*

(Continued)

*Primary Examiner* — James M Mellott
(74) *Attorney, Agent, or Firm* — Birch, Stewart, Kolasch & Birch, LLP

(57) ABSTRACT

The objective of the present invention is to provide a cleaning agent composition which can be used in the open air without any problems since the cleaning agent is environmentally friendly and which is effective for removing a low-molecular-weight and poorly-water-soluble cyclic sili- (Continued)

cone compound that causes a stain of a silicone sealing. The cleaning agent for washing out a silicone stain according to the present invention is characterized in comprising a cyclic lipopeptide biosurfactant, wherein the specific silicone stain compound such as D4 compound is the objective compound to be removed.

16 Claims, 1 Drawing Sheet

(56) References Cited

U.S. PATENT DOCUMENTS

2005/0032677 A1    2/2005    Kitakuni et al.
2013/0072414 A1*   3/2013    Price ........................ C11D 1/37
                                                                              510/220

FOREIGN PATENT DOCUMENTS

| JP | 2004-149448 A | 5/2004 |
|----|---------------|--------|
| JP | 2010-285812 A | 12/2010 |
| WO | WO 2012/098278 A1 | 7/2012 |

OTHER PUBLICATIONS

International Search Report, issued in PCT/JP2014/058228, dated Jun. 17, 2014.

Yoneda et al., "Surfactin sodium salt: an excellent bio-surfactant for cosmetics", Research Report, Fragrance Journal, 2001, vol. 29, No. 12, pp. 93-97 (9 pages total).

* cited by examiner

CLEANING AGENT FOR WASHING OUT SILICONE STAIN

TECHNICAL FIELD

The present invention relates to a cleaning agent which is used for washing out a silicone stain and which is environmentally friendly. In particular, the cleaning agent is effective against the stain caused by a silicone sealant. The present invention also relates to a method for removing a silicone stain using the cleaning agent for washing out the silicone stain, and a method for replacing a silicone sealant.

BACKGROUND ART

A silicone sealant is generally a product prepared by crosslinking a linear polysiloxane having the following formula with a crosslinking agent.

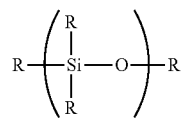

wherein 'R's are independently a hydrogen atom, a $C_{1-6}$ alkyl group or the like, and the polymerization degree is up to about 500.

In more detail, when a crosslinking agent is allowed to act on the above-described linear polysiloxane, Si—R is thereby converted to Si—OH and then a dehydration condensation reaction occurs between Si—OH groups of linear molecules to form a siloxane linkage, and thus the linear polysiloxanes are crosslinked. As a result, the polysiloxane becomes insolubilized to be a sealant having moderate elasticity.

However, a polysiloxane chain is broken due to a side reaction caused by a crosslinking agent, and for example, the following by-product compound in which four —SiR$_2$—O— are linked in a cyclic form is produced. The following compound is an example of the case where all of 'R' groups are methyl groups.

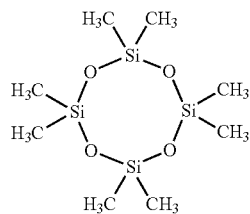

The above compound is referred to as D4. Similarly, D5, which is composed of five units, D6, which is composed of six units, and the like are known. The by-product compounds exhibit slight water solubility and therefore elutes from a sealing due to rain or the like. For example, the by-product compounds raise a problem that the compounds cause a stain below the sealing. As one example, a photograph showing the appearance of a building is shown in FIG. 1. As shown in FIG. 1, a by-product compound has oozed out from a silicone sealant between outer wall panels and has stained each outer wall panel from the periphery part toward the central part.

There are some silicone sealant products of which content of such a by-product compound is reduced; however, the above-mentioned side reaction occurs and D4 or the like is formed after use as long as a crosslinking agent remains even in a slight amount. The formed by-product compound will bleed out to the surface of a sealing and is eluted by rain or the like as described above to cause a stain or the like.

The above-described by-product compound that have eluted and have become stain cannot be removed with an ordinary cleaning agent, and an acidic cleaning agent should be used to remove the stain. However, a strong acidic cleaning agent for removing the by-product compound should not be used, since such an agent is dangerous for cleaning personnel and also causes environmental pollution.

Patent Document 1 discloses a cleaning agent for a silicon wafer production process. The cleaning agent contains an anionic surfactant having a weight-average molecular weight of 600 to 200,000, a silicone-based surfactant and an alkali. Patent Document 2 discloses a cleaning composition which contains an anionic surfactant and a cationic polymer and which exhibits high detergency against a stain of a silicone oil and the like.

PRIOR ART DOCUMENT

Patent Document

Patent Document 1: JP 2010-285612 A
Patent Document 2: JP H6-16534 A

DISCLOSURE OF THE INVENTION

Problems to be Solved by the Invention

Since the above-described by-product compound which is contained in a silicone sealant may cause a stain of a building material and the like, a cleaning agent which is effective against such a stain has been required. However, no practically useful product is currently available.

A cleaning agent for a silicon wafer production process is disclosed in Patent Document 1. However, the cleaning agent is a product for removing a slurry in which an abrasive grain, a silicon dust and the like are mixed and dispersed in a cutting fluid for a silicon wafer, and is not a product for removing a cyclic siloxane having a relatively low molecular weight. On the one hand, the composition disclosed in Patent Document 2 is a product for removing a stain due to silicone oil and the like. However, the silicone oil disclosed as an object to be removed is mainly oily silicone oil such as decamethylcyclopentasiloxane and dimethylpolysiloxane, and the composition is not a product which is developed for removing a low-molecular-weight cyclic siloxane. In addition, the composition cannot be practically used for washing outer wall of a building, since the composition produces an excessively large environmental load.

Under the above-described circumstances, the objective of the present invention is to provide a cleaning agent composition which can be used in the open air without any problems since the cleaning agent is environmentally friendly and which is effective for removing a low-molecular-weight and poorly-water-soluble cyclic silicone compound that causes a stain of a silicone sealing.

Means for Solving the Problems

The inventors of the present invention repeated intensive studies in order to solve the above-described problems. As a result, the inventors completed the present invention by finding that a cyclic lipopeptide biosurfactant, which is a naturally occurring surfactant, is very effective in removal of a cyclic silicone compound to be removed, and that there is no need to recover the surfactant after use since the surfactant is a peptide compound, which is easily decomposed in nature, and therefore the surfactant can be used in the open air in a large scale.

Hereinafter, the present invention is described.

[1] A cleaning agent for washing out a silicone stain, comprising a cyclic lipopeptide biosurfactant, wherein the silicone stain to be washed out is a cyclic silicone compound represented by the following formula (I):

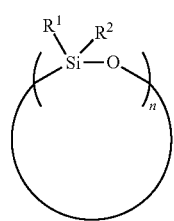

(I)

wherein $R^1$ and $R^2$ are independently a hydrogen atom, a $C_{1-6}$ alkyl group, a $C_{2-6}$ alkenyl group or a $C_{6-10}$ aryl group; 'n' is an integer of not less than 4 and not more than 8.

[2] The cleaning agent for washing out a silicone stain according to the above [1], wherein the cyclic lipopeptide biosurfactant is a surfactin salt represented by the following formula (II):

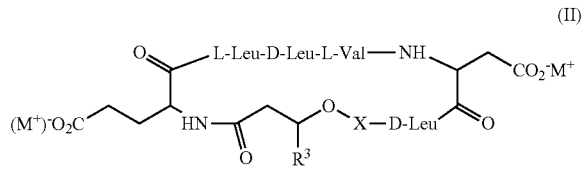

(II)

wherein 'X' is a residue of an amino acid selected from leucine, isoleucine and valine; $R^3$ is a $C_{9-18}$ alkyl group; '$M^+$' is an alkali metal ion or a quaternary ammonium ion.

[3] The cleaning agent for washing out a silicone stain according to the above [1] or [2], wherein the cyclic lipopeptide biosurfactant is dissolved in an aqueous solvent, and the concentration thereof is not less than 0.003% by mass.

[4] The cleaning agent for washing out a silicone stain according to any one of the above [1] to [3], wherein the cyclic lipopeptide biosurfactant is dissolved in an aqueous solvent, and the concentration thereof is not more than 10% by mass.

[5] The cleaning agent for washing out a silicone stain according to the above [3] or [4], wherein the aqueous solvent is a mixed solvent of a water-miscible organic solvent and water.

[6] The cleaning agent for washing out a silicone stain according to any one of the above [1] to [5], wherein $R^1$ and $R^2$ are methyl groups.

[7] The cleaning agent for washing out a silicone stain according to the above [2], wherein at least one of '$M^+$' is a sodium ion.

[8] A method for removing a silicone stain, comprising the step of washing out the silicone stain adhered on the surface of an object by the cleaning agent for washing out a silicone stain according to any one of the above [1] to [7].

[9] The method according to the above [8], wherein the object adhered by the silicone stain on the surface is a glass or an exterior wall.

[10] The method according to the above [9], wherein the exterior wall is a marble board, a concrete board, a brick, a roofing tile, a ceramic tile, a metal board, a flame-retardant plyboard, a ceramic siding board or an enamel panel.

[11] The method according to any one of the above [8] to [10], further comprising the step of removing the cleaning agent for washing out a silicone stain after the washing step.

[12] The method according to any one of the above [8] to [11], comprising the step of scrubbing the surface of the object in the washing step.

[13] A method for replacing a silicone sealant, comprising the steps of physically removing the silicone sealant, washing the silicone sealant-removed part by the method according to any one of the above [8] to [12], and applying a new sealant on the washed silicone sealant-removed part.

Effect of the Invention

The cleaning agent according to the present invention makes it possible to effectively remove a silicone-derived and poorly-water-soluble stain compound such as D4 to D6, for which no effective cleaning agent has heretofore been known. In addition, since the cyclic lipopeptide biosurfactant that is a main component of the cleaning agent according to the present invention is a naturally occurring peptide surfactant, the surfactant is rapidly decomposed by microorganisms or the like even if the surfactant is used to be released to the environment. The biosurfactant therefore can be used in the open air in a large amount, since the biosurfactant gives only a little load on the environment. Furthermore, if the above-described poorly-water-soluble stain compound remains, the adhesiveness between the remained part and a new sealant is degraded; on the one hand, when the poorly-water-soluble stain compound is washed and removed using the cleaning agent of the present invention, the adhesiveness to a new sealant is improved. Accordingly, the cleaning agent of the present invention is industrially very useful as an agent effective for washing of a building outer wall and the like to which a silicone sealant is applied and for replacing an existing silicone sealant with a new sealant.

BRIEF DESCRIPTION OF THE DRAWINGS

FIG. 1 is a photograph showing one example of an outer wall soiled by a poorly-water-soluble stain which is derived from a silicone sealant.

MODE FOR CARRYING OUT THE INVENTION

The objective compound to be removed by the cleaning agent for washing out a silicone stain according to the present invention is the following cyclic silicone compound (I), for which no effective cleaning agent has heretofore been known:

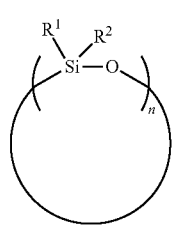 (I)

wherein $R^1$ and $R^2$ are independently represent a hydrogen atom, a $C_{1-6}$ alkyl group, a $C_{2-6}$ alkenyl group or a $C_{6-10}$ aryl group; and 'n' is an integer of not less than 4 and not more than 8.

In the present invention, the term "$C_{1-6}$ alkyl group" is a linear or branched monovalent saturated aliphatic hydrocarbon group having not less than 1 and not more than 6 carbon atoms. The example thereof includes methyl, ethyl, n-propyl, isopropyl, n-butyl, isobutyl, s-butyl, t-butyl, n-pentyl and n-hexyl. As the group, a $C_{1-4}$ alkyl group is preferred, a $C_{1-2}$ alkyl group is more preferred, and methyl is particularly preferred.

The term "$C_{2-6}$ alkenyl group" is a linear or branched monovalent unsaturated aliphatic hydrocarbon group which has one or more carbon-carbon double bond and which has not less than 2 and not more than 6 carbon atoms. The example thereof includes ethenyl, allyl, isopropenyl, 1-butenyl, 2-butenyl, isobutenyl, 1,3-pentadienyl and 1,3,5-hexatrienyl. As the group, a $C_{2-4}$ alkenyl group is preferred, a $C_{2-3}$ alkenyl group is more preferred, and allyl is particularly preferred.

The term "$C_{6-10}$ aryl group" is a monovalent aromatic hydrocarbon group having not less than 6 and not more than 10 carbon atoms. The example thereof includes phenyl, indenyl, and naphthyl, and phenyl is preferred.

The 'n' is preferably not more than 6, and D4 compound of which 'n' is 4 is the most problematic as a stain compound.

The cleaning agent for washing out a silicone stain according to the present invention contains a cyclic lipopeptide biosurfactant as an active ingredient which is effective for removal of the cyclic silicone compound (I) by emulsification.

The cyclic lipopeptide biosurfactant is a cyclic peptide which has a lipophilic group such as a long chain alkyl group and which exhibits a surfactant activity. The cyclic lipopeptide biosurfactant is excellent in an effect of cleaning and removing the cyclic silicone compound (I), and is also advantageous in that the biosurfactant is extremely high in biodegradability and gives only a little influence on a living body and the environment since the biosurfactant is a peptide compound.

The cyclic lipopeptide biosurfactant is not particularly restricted as long as the biosurfactant is a peptide compound which has a bulky cyclic structure and which is capable of exhibiting a surfactant activity. The example thereof includes surfactin, arthrofactin, iturin, serrawettin, lichenysin and viscosin.

In the present invention, a surfactin salt represented by the following formula (II) can be suitably used as the cyclic lipopeptide biosurfactant.

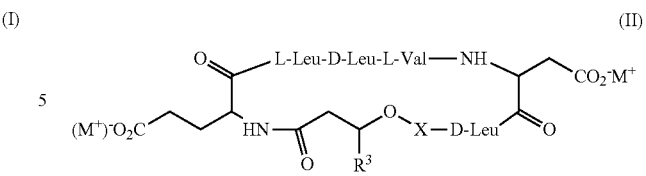 (II)

wherein
'X' is a residue of an amino acid selected from leucine, isoleucine and valine;
$R^3$ is a $C_{9-18}$ alkyl group;
'$M^+$' is an alkali metal ion or a quaternary ammonium ion.

Although the amino acid residue as 'X' may be either in a L-form or a D-form, the L-form is preferred.

The term "$C_{9-18}$ alkyl group" means a linear or branched monovalent saturated hydrocarbon group having not less than 9 and not more than 18 carbon atoms. The example thereof includes n-nonyl, 6-methyloctyl, 7-methyloctyl, n-decyl, 8-methylnonyl, n-undecyl, 9-methyldecyl, n-dodecyl, 10-methylundecyl, n-tridecyl, 11-methyldodecyl, n-tetradecyl, n-pentadecyl, n-hexadecyl, n-heptadecyl and n-octadecyl.

The alkali metal ion is not particularly restricted and represents a lithium ion, a sodium ion, a potassium ion or the like. The two alkali metal ions may be either the same or different from each other. In addition, one of the —$CO_2^-M^+$ units may be in the state of —COOH.

The example of a substituent of the quaternary ammonium ion includes an organic group, for example, an alkyl group such as methyl, ethyl, n-propyl, isopropyl, n-butyl and tert-butyl; an aralkyl group such as benzyl, methylbenzyl and phenylethyl; and an aryl group such as phenyl, toluyl and xylyl. The quaternary ammonium ion is exemplified by a tetramethylammonium ion, a tetraethylammonium ion and a pyridinium ion.

Either one of the surfactin salts or two or more salts may be used.

A cyclic lipopeptide biosurfactant is a naturally-occurring surfactant and therefore can be isolated from a microorganism itself which produces the cyclic lipopeptide biosurfactant or a culture broth thereof. For example, the surfactin salt (II) can be isolated from a culture broth prepared by culturing a microorganism such as a strain belonging to Bacillus subtilis in accordance with a known method. The cyclic lipopeptide biosurfactant may be a purified product or an unpurified product. Such an unpurified product is exemplified by a culture broth as it is. The product of the surfactin salt obtained by a chemical synthesis method may be similarly used.

In the cleaning agent for washing out a silicone stain according to the present invention, the cyclic lipopeptide biosurfactant preferably exists in a state of being dissolved in an aqueous solvent in a concentration of not less than 0.003% by mass and not more than 10% by mass. When the concentration is not less than 0.003% by mass, the cyclic lipopeptide biosurfactant can sufficiently form a micelle in the solution, and it becomes possible to entrap a silicone stain in the micelle and to remove the silicone stain more certainly. On the one hand, the concentration is preferably not more than 10% by mass since the effect may possibly become saturated if the concentration is excessively high. The concentration is more preferably not more than 7.5% by mass, even more preferably not more than 5% by mass, still even more preferably not more than 2.5% by mass, and particularly preferably not more than 1.0% by mass.

The cleaning agent for washing out a silicone stain according to the present invention is preferably in a liquid state but may be in a solid state and may also be in a semi-solid state having flowability, such as gel. However, since the cleaning agent for washing out a silicone stain according to the present invention removes the cyclic silicone compound (I) by the cyclic lipopeptide biosurfactant, which is a surfactant, when the cleaning agent is in a solid state or in a semi-solid state, the cleaning agent is mixed to be dissolved in an aqueous solvent at least before use. Moreover, in the case where the cleaning agent is in a semi-solid state having flowability, washing is carried out in the presence of an aqueous solvent after the cleaning agent is applied to a stained portion.

In the present invention, the aqueous solvent means water alone, a water-miscible organic solvent alone, or a mixed solvent of water and a water-miscible organic solvent.

The kind of water in the present invention is not particularly restricted, and any kind of water, such as distilled water, pure water, ultrapure water, purified water, tap water and well water, can be used.

The water-miscible organic solvent is not particularly restricted as long as the solvent is miscible with water at ordinary temperature and does not give an excessive load on the environment, and the example thereof includes an alcohol solvent such as methanol, ethanol and isopropanol; an ether solvent such as tetrahydrofuran; and a ketone solvent such as acetone.

As the solvent of the cleaning agent for washing out a silicone stain, a mixed solvent of water and a water-miscible organic solvent is particularly preferred. The cleaning agent for washing out a silicone stain which agent contains such a mixed solvent is particularly superior in an action to wash out the cyclic silicone compound (I). A ratio of the water-miscible organic solvent in the mixed solvent is preferably not less than 5 v/v % and not more than 50 v/v %. When the ratio is not less than 5 v/v %, an effect due to the water-miscible organic solvent to improve the washing action against the cyclic silicone compound (I) can be obtained more certainly. On the one hand, when the ratio is excessively high, a bad influence may be possibly given to the environment even if the water-miscible organic solvent is relatively safe. The ratio is therefore preferably not more than 50 v/v %. The ratio is more preferably not less than 10 v/v %, even more preferably not less than 15 v/v %, and more preferably not more than 40 v/v %, even more preferably not more than 30 v/v %.

To the cleaning agent for washing out a silicone stain according to the present invention, a component which is commonly added to a cleaning agent may be additionally added.

For example, when there is a stain compound to be removed other than the cyclic silicone compound (I), such an additional component may be selected appropriately depending upon the kind or the like of the stain compound. For example, it is possible to add an anionic surfactant other than the cyclic lipopeptide biosurfactant, a cationic surfactant, a nonionic surfactant and an amphoteric surfactant.

The example of the anionic surfactant other than the cyclic lipopeptide biosurfactant includes a sulfuric acid ester salt surfactant such as sodium lauryl sulfate and sodium polyoxyethylene lauryl ether sulfate. The example of the cationic surfactant includes a quaternary ammonium salt surfactant such as distearyldimethylbenzylammonium chloride and benzalkonium chloride. The example of the nonionic surfactant includes a sugar fatty acid ester surfactant such as a sucrose fatty acid ester. The example of the amphoteric surfactant includes an acetic acid betaine surfactant such as betaine lauryldimethylaminoacetate and coconut oil fatty acid amide propyldimethylamino acetic acid betaine. Only one kind of the above surfactant may be selected to be used or alternatively two or more above surfactans may be selected to be used in combination in addition to the cyclic lipopeptide biosurfactant.

A cleaning aid may be added to the cleaning agent for washing out a silicone stain according to the present invention. The example of the cleaning aid includes a dicarboxylic acid and a salt thereof, such as succinic acid, glutaric acid and malonic acid; an aminocarboxylic acid and a salt thereof, such as ethylenediaminetetraacetic acid and hydroxyethylenediamineacetic acid; and a phosphoric acid compound and a salt thereof, such as orthophosphoric acid, trimetaphosphoric acid, pyrophosphoric acid and tripolyphosphoric acid. The example of the salt includes an alkali metal salt such as a sodium salt and a potassium salt; and an ammonium salt.

As the cleaning aid, an alkaline agent may also be used, and the example of the alkaline agent includes a hydroxide such as sodium hydroxide and potassium hydroxide; a carbonate such as sodium carbonate, potassium carbonate and sodium sesquicarbonate; a borate such as potassium borate and sodium borate; a hydrogensulfate such as sodium hydrogensulfate and potassium hydrogensulfate; an inorganic alkali metal salt such as sodium silicate, sodium metasilicate, potassium silicate, potassium metasilicate and zeolite; an organic alkali metal salt such as sodium formate, sodium acetate and sodium oxalate; and an organic amine such as triethylamine. However, since the alkaline agent may possibly have a bad influence on the environment, it is preferred not to add a strong base and the amount thereof should be controlled.

An amount of the cleaning aid to be added may be adjusted appropriately and for example, the ratio thereof to the cyclic lipopeptide biosurfactant may be adjusted to not less than 0.01 parts by mass and not more than 5 parts by mass.

When a polyvalent metal ion such as a calcium ion or a magnesium ion exists on the object to be washed, the cyclic lipopeptide biosurfactant may be possibly deactivated. In such a case, the above-described alkaline agent is effective, but the alkaline agent may have a bad influence on the environment. Accordingly, in such a case, it is preferred to add a chelating agent for scavenging a polyvalent metal ion.

The example of the chelating agent includes an edetic acid or a salt thereof, such as EDTA or a sodium salt thereof; a hydroxyethylethylenediamine triacetic acid or a salt thereof, such as HEDTA or a sodium salt thereof; pentetic acid or a salt thereof; phytic acid; a phosphonic acid such as etidronic acid, and a salt thereof such as a sodium salt; an organic acid or a salt thereof, such as oxalic acid, citric acid, alanine, dihydroxyethylglycine, gluconic acid, ascorbic acid, succinic acid and tartaric acid; and a polyamino acid such as polyaspartic acid and polyglutamic acid. Among the examples, in consideration of the environmental impact, an organic acid or a salt thereof, such as sodium citrate, is preferred.

In addition, the cleaning agent for washing out a silicone stain according to the present invention is allowed to contain a polyhydric alcohol such as ethylene glycol and propylene glycol; a low temperature stabilizer, for example, a lower alkylsulfonic acid salt such as a benzenesulfonic acid salt and a toluenesulfonic acid salt; an antioxidant such as 2,6-di-t-butyl-p-cresol, 2,6-diphenyl-4-octadecyloxyphenol, 2,5-di-t-butylhydroquinone and DL-α-tocopherol; an antiseptic agent such as a p-hydroxybenzoic acid ester; a fragrance; a dye and the like.

The present invention also relates to a method for removing a silicone stain, characterized in comprising the step of washing out the cyclic silicone compound (I) which is adhered on the surface of an object by the cleaning agent according to the present invention. Hereinafter, the method is described step by step.

Step (A): Washing Step

The poorly-water-soluble cyclic silicone compound (I) formed as a by-product in a silicone compound such as a silicone sealant bleeds out or is eluted from the silicone compound slightly with time to stain the silicone compound itself or the surrounding thereof. In the present step, the cyclic silicone compound (I) that causes a stain is removed by being washed with the cleaning agent for washing out a silicone stain according to the present invention.

The object of which surface is stained by the cyclic silicone compound (I) is exemplified by a glass or an exterior wall to which a silicone sealant is applied or which is located around a silicone sealant. The exterior wall is not particularly restricted, and is exemplified by a marble plate; a concrete plate such as a fiber-reinforced cement plate and a cemented excelsior plate; a brick; a roofing tile; a ceramic tile; a metal plate such as a steel plate and an aluminum plate; a flame retardant plywood; a ceramic siding; and an enamel panel. In the present invention, the above-described plate includes ones having a relatively small plane area like that called a block and relatively thick one.

The method of washing the object is not particularly restricted, and a conventional method can be used. The example thereof includes the following methods:

the cleaning agent for washing out a silicone stain is applied to the surface of the object on which surface the cyclic silicone compound (I) is adhered with a spray or the like;

a brush or a waste cloth is impregnated with the cleaning agent for washing out a silicone stain and the surface of the object is polished using the brush or waste cloth; and a waste cloth is impregnated with the cleaning agent for washing out a silicone stain and applied to the surface of the object, followed by leaving the cloth at rest for a certain period of time.

A specific cleaning condition and cleaning time may be set in such a manner that the cyclic silicone compound (I) to be removed can be sufficiently solubilized from the object surface.

In the present step, it is preferred that the surface of the object is treated with the cleaning agent for washing out a silicone stain and then polished in order to effectively remove the cyclic silicone compound (I) from the object surface. For example, it is preferred to impregnate a brush or a waste cloth with the cleaning agent for washing out a silicone stain and polish the object surface therewith as described above. Alternatively, in the case where the cleaning agent for washing out a silicone stain is applied to the object surface or a waste cloth impregnated with the cleaning agent for washing out a silicone stain is applied to the object surface in the present step, it is preferred to subsequently polish the object surface sufficiently with a brush or the like. However, when the object is a glass, the cyclic silicone compound (I) can be sufficiently removed even if the following removal step is carried out without polishing the surface of the glass.

Step (B): Removing Step

It is preferred to remove the cyclic silicone compound (I) together with the cleaning agent for washing out a silicone stain after the above-described washing step (A). In such a case, since the cyclic silicone compound (I) is solubilized by the cleaning agent for washing out a silicone stain, the compound can be easily removed.

The means for the removal is not particularly restricted, and for example, an aqueous solvent such as water is sprayed to the object surface or a squeezee is used.

Even if the cleaning agent for washing out a silicone stain is released to the environment during the present step, a load on the environment is considered to be small since the cyclic lipopeptide biosurfactant as an active ingredient of the cleaning agent is biodegradable.

In addition, the present invention relates to a method for replacing a silicone sealant, characterized in comprising the steps of physically removing the silicone sealant, washing the silicone sealant-removed part by the above-described method for removing a silicone stain, and applying a new sealant on the washed silicone sealant-removed part. Hereinafter, the method is described step by step.

Step (C): Step of Removing Silicone Sealant

It is necessary to replace a silicone sealant, since a silicone sealant is generally degraded with time or soiled due to generation of a mold on a surface thereof. Accordingly, first, an old silicone sealant is physically removed in the present step.

The method of physically removing an old silicone sealant is exemplified by cutting with a cutter or the like. Although most of the silicone sealant can be removed by the method, the silicone sealant remains partly, especially at the adhesion part with a base. It is therefore preferred to further remove the remaining silicone sealant by polishing after swelling the silicone sealant with a silicone remover, for example.

Step (D): Washing Step

In the present step, a portion from which a silicone sealant is removed by the above-described method of removing a silicone stain is washed.

In general, the cyclic silicone compound (I) remains even if an old silicone sealant is removed as in the step (C). As a result, a newly applied sealant tends to peel off easily due to poor adhesiveness between the removal surface and the new sealant. However, since the remaining cyclic silicone compound (I) can be removed by washing the portion from which the silicone sealant is removed by the method for removing a silicone stain according to the present invention, the adhesiveness with a new sealant is improved and a newly applied sealant becomes hard to peel off.

Step (E): Applying Step

After washing the portion from which the silicone sealant is removed by the above-described step (D), a new sealant is applied. A conventional method can be used as the application method.

As described above, when the portion from which an old silicone sealant is removed is washed by the method of the present invention, the adhesiveness with a new sealant is improved and the newly applied sealant becomes hard to peel off.

The new sealant to be used may be the same as or different from the removed silicone sealant.

The present application claims the benefit of the priority date of Japanese patent application No. 2013-62835 filed on Mar. 25, 2013. All of the contents of the Japanese patent application No. 2013-62835 filed on Mar. 25, 2013, are incorporated by reference herein.

EXAMPLES

Hereinafter, the present invention is described in more detail with Examples. However, the present invention is not restricted to the following Examples in any way, and it is possible to work the present invention according to the Examples with an additional appropriate change within the range of the above descriptions and the following descriptions. Such a changed embodiment is also included in the technical scope of the present invention.

Example 1

To 4 mL of water, 100 μL ($8 \times 10^{-2}$ M) of D4 compound, which was a cyclic silicone compound, was added. The mixture was stirred. Further, sodium surfactin or SDS, i.e. sodium lauryl sulfate, was added thereto in the concentrations shown in Table 1. The mixture was stirred again and the emulsion status of D4 compound was observed. The emulsion status was checked by irradiating a mixed aqueous solution with light and measuring the absorbance of light having a wavelength of 620 nm. A higher absorbance indicates that D4 compound was dispersed more finely and was in an emulsified state. The obtained results are demonstrated in Table 1.

TABLE 1

| Experiment No. | Surfactant concentration [mM] | Example Sodium surfactin [absorbance at 620 nm] | Comparative example Sodium lauryl sulfate [absorbance at 620 nm] |
|---|---|---|---|
| 1 | 0.001 | 0.05 | 0.02 |
| 2 | 0.005 | 0.20 | 0.02 |
| 3 | 0.010 | 0.30 | 0.04 |
| 4 | 0.050 | 0.70 | 0.04 |
| 5 | 0.100 | 0.70 | 0.04 |
| 6 | 0.250 | 0.90 | 0.04 |
| 7 | 0.500 | 0.90 | 0.04 |
| 8 | 0.750 | 0.90 | 0.03 |
| 9 | 1.000 | 0.50 | 0.02 |
| 10 | 2.500 | 0.50 | 0.04 |
| 11 | 5.000 | 0.20 | 0.03 |
| 12 | 7.500 | 0.20 | 0.05 |
| 13 | 10.000 | 0.10 | 0.02 |
| 14 | 25.000 | 0.10 | 0.03 |

From the result shown in Table 1, it can be found that in the case of sodium lauryl sulfate, which is a typical anionic surfactant widely used due to high versatility, an emulsified state could not be formed for D4 compound at any concentrations, and the absorbance was kept low and D4 compound was not emulsified even at 7.5 mM, which is higher than the critical micelle concentration of sodium lauryl sulfate.

On the one hand, when sodium surfactin was used, it was experimentally demonstrated that although sodium surfactin is classified into an anionic surfactant as sodium lauryl sulfate, a high emulsifying capability for D4 compound could be exhibited, since a high absorbance was measured in a wide concentration range exceeding 0.003 mM, which is the critical micelle concentration of sodium surfactin. The result reveals that a sodium surfactin solution having a concentration exceeding 0.003 mM has a high washing capability for D4 compound, which is a stain compound. It is however noted that the absorbance rather lowered when the concentration of sodium surfactin was 1 mM or more. Although the reason for the result is not clear, the fact that sedimentation or the like of D4 compound was not observed may indicate that a finer micelle was formed to lower the turbidity, or a part of D4 compound started to be completely dissolved to increase transparency.

Example 2

A silicone sealant ("DOW CORNING (registered trademark) 791 SILICONE WEATHERPROOFING SEALANT" produced by Dow Corning Corporation) was applied to a glass plate having a size of 150 mm×70 mm, and then the applied plate was left at rest under a condition of 23° C. and 50% RH for 10 days. Subsequently, a cycle of applying water with a shower for 5 minutes followed by heating within a dryer at 50° C. for 55 minutes was repeated four times in order to generate a silicone stain from the silicone sealant. The resultant was used as a silicone-stained glass plate.

Cleaning liquids were prepared by dissolving sodium surfactin (SF) in water, ethanol (EtOH), acetone, isopropanol (IPA), a 20 v/v % aqueous solution of ethanol, a 20 v/v % aqueous solution of acetone or a 20 v/v % aqueous solution of isopropanol in a concentration of 1.0 wt %. Each cleaning liquid was put in a commercially available sprayer container, and 3 mL thereof was sprayed to a central portion of the silicone-stained glass plate. The cleaning liquid was spread using a sponge across the entire surface of the glass plate, and then the liquid was removed with a squeezee. For comparison, experiments were also carried out in a similar manner except that a solvent alone was used without adding sodium surfactin or sodium lauryl sulfate (SDS) was used instead of sodium surfactin. Since a silicone stain compound is low in water solubility and exhibits water repellency, water was dropped on the washed glass and the degree of water repellency was visually observed. From the result, the degree of removing stain was evaluated according to the following criteria. The results are demonstrated in Table 2.

Very good: the washed glass plate exhibited water repellency comparable to that of the raw material glass plate.

Good: the washed glass plate exhibited slightly higher water repellency than the material glass plate.

Bad: the washed glass plate exhibited slightly lower water repellency than the unwashed glass plate.

Very bad: the water repellency did not differ before and after washing.

TABLE 2

| | | Solvent | | | | | | |
|---|---|---|---|---|---|---|---|---|
| | | Water | EtOH | 20% EtOH aq | Acetone | 20% Acetone aq | IPA | 20% IPA aq |
| Solute | SF 1.0 wt % | bad | good | very good | good | very good | good | very good |
| | — | very bad | very bad | bad | bad | bad | bad | bad |
| | SDS 1.0 wt % | very bad | very bad | bad | bad | bad | bad | bad |

As shown by the result given in Table 2, a silicone stain could be removed more effectively by a sodium surfactin solution than a solvent alone or a sodium lauryl sulfate solution. The effect was high especially when a mixed solvent of water and a water-miscible organic solvent was used.

In addition, the same washing operation as described above was carried out using a 20 v/v % aqueous solution of ethanol as a solvent with variation in sodium surfactin concentration, and then the contact angle of water was measured to evaluate an effect of washing and removing a silicone stain. The result is demonstrated in Table 3.

TABLE 3

| | SF concentraion in 20% EtOH aq (wt %) | | | | |
|---|---|---|---|---|---|
| | 0.00 | 0.05 | 0.10 | 0.50 | 1.00 |
| Contact angle | 83.8° | 76.6° | 70.1° | 72.4° | 75.8° |

In Table 3, a smaller contact angle means that water repellency was lower, in other words, that a silicone stain was removed. It is therefore revealed that a silicone stain can be washed and removed effectively by adding sodium surfactin to a cleaning liquid.

Example 3

A silicone sealant ("DOW CORNING (registered trademark) 791 SILICONE WEATHERPROOFING SEALANT" produced by Dow Corning Corporation) was applied to an aluminum plate, and then the applied plate was left at rest in a condition of 23° C. and 50% RH for 10 days. Subsequently, a part of the silicone sealant was removed using a scraper while the other part of the sealant was left in a thickness of about 1 mm. The remaining silicone sealant was swollen with a commercially available limonene cleaning liquid, and then the removal surface was wiped with a rag. Subsequently, a rag was impregnated with an solution which was prepared by dissolving sodium surfactin in 20 v/v % aqueous solution of ethanol or a 20 v/v % aqueous solution of acetone in a concentration of 1.0 wt %, and the surface from which the silicone sealant had been removed was polished therewith for 30 seconds, followed by wiping with a rag impregnated with only the corresponding solvent. The contact angle of water was measured before the application of the silicone sealant, and before and after the washing operation with the SF solution. The result is demonstrated shown in Table 4.

TABLE 4

| | Before coating sealant | Before washing procedure | After washing with SF solution in EtOH aq | After washing with SF solution in acetone aq |
|---|---|---|---|---|
| Contact angle | 91° | 113° | 93° | 100° |

As the result given in Table 4, it can be found that although a commercially available cleaning liquid could also remove a sealant itself, a silicone stain remained on the removal surface, and the surface of the aluminum plate became water-repellent. However, it is believed that a silicone stain could be removed by washing a surface from which a silicone sealant had been removed with sodium surfactin, and as a result, adhesiveness when a new sealant was applied could be improved.

The invention claimed is:

1. A method for removing a silicone stain, comprising the step of washing out the silicone stain adhered on the surface of an object, wherein the silicone stain to be washed out is a cyclic silicone compound represented by the following formula (I):

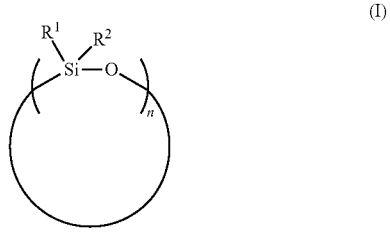

(I)

wherein $R^1$ and $R^2$ are independently a hydrogen atom, a $C_{1-6}$ alkyl group, a $C_{2-6}$ alkenyl group, or a $C_{6-10}$ aryl group and 'n' is an integer of not less than 4 and not more than 8, by a cleaning agent comprising a surfactin salt represented by the following formula (II):

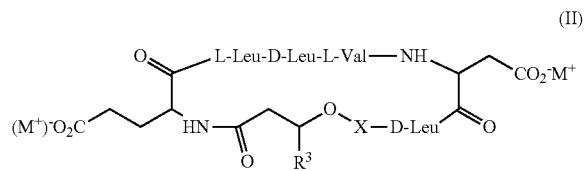

(II)

wherein 'X' is a residue of an amino acid selected from leucine, isoleucine, and valine, $R^3$ is a $C_{9-18}$ alkyl group, and '$M^+$' is an alkali metal ion or a quaternary ammonium ion.

2. The method according to claim 1, wherein the object adhered by the silicone stain on the surface is a glass or an exterior wall.

3. The method according to claim 2, wherein the exterior wall is a marble board, a concrete board, a brick, a roofing tile, a ceramic tile, a metal board, a flame-retardant plyboard, a ceramic siding board or an enamel panel.

4. The method according to claim 1, further comprising the step of removing the cleaning agent for washing out a silicone stain after the washing step.

5. The method according to claim 1, comprising the step of scrubbing the surface of the object in the washing step.

6. A method for replacing a silicone sealant, comprising the steps of
physically removing the silicone sealant,
washing the silicone sealant-removed part by the method according to claim 1, and
applying a new sealant on the washed silicone sealant-removed part.

7. The method according to claim 1, wherein the surfactin salt is dissolved in an aqueous solvent, and the concentration thereof in the cleaning agent is not less than 0.003% by mass.

8. The method according to claim 7, wherein the aqueous solvent is water, a water-miscible organic solvent, or a mixed solvent of water and a water-miscible organic solvent.

9. The method according to claim 8, wherein the water-miscible organic solvent is an alcohol solvent, an ether solvent, or a ketone solvent.

10. The method according to claim 1, wherein the surfactin salt is dissolved in an aqueous solvent, and the concentration thereof is not more than 10% by mass.

11. The method according to claim 10, wherein the aqueous solvent is water, a water-miscible organic solvent, or a mixed solvent of water and a water-miscible organic solvent.

12. The method according to claim 11, wherein the water-miscible organic solvent is an alcohol solvent, an ether solvent, or a ketone solvent.

13. The method according to claim 1, wherein $R^1$ and $R^2$ are methyl groups.

14. The method according to claim 1, wherein at least one of '$M^+$' is a sodium ion.

15. The method according to claim 1, wherein 'n' is an integer of not less than 4 and not more than 6.

16. The method according to claim 1, wherein a concentration of the surfactin salt in the cleaning agent is no more than 5% by mass.

* * * * *